United States Patent [19]

Dawson

[11] 3,965,008
[45] June 22, 1976

[54] PORTABLE WATER STERILIZATION DEVICE

[76] Inventor: Gerald C. Dawson, 391 Silvera Ave., Long Beach, Calif. 90814

[22] Filed: May 8, 1975

[21] Appl. No.: 575,485

Related U.S. Application Data

[63] Continuation-in-part of Ser. No. 451,576, March 15, 1974, abandoned.

[52] U.S. Cl. .............................. 210/192; 210/232; 210/243; 210/250; 21/102 R; 204/308
[51] Int. Cl.² ........................................ B01D 21/00
[58] Field of Search ............ 210/71, 192, 205, 250, 210/243, 232; 21/102 R; 204/308

[56] References Cited
UNITED STATES PATENTS

| | | | |
|---|---|---|---|
| 1,123,117 | 12/1914 | Ewing | 210/250 X |
| 1,432,124 | 10/1922 | Rudd | 204/308 |
| 3,296,122 | 1/1967 | Karassik et al. | 210/71 X |

*Primary Examiner*—John Adee
*Attorney, Agent, or Firm*—William C. Babcock

[57] ABSTRACT

A light weight portable device for sterilizing harmful bacteria containing water by the use of commercial alternating electric current. The components of the device are removably connected to one another, and may be separated and stored in a compact arrangement when the device is not in use. The device is particularly adapted for supplying potable water from contaminated water in areas that have been subjected to a disaster such as a flood, earthquake or the like. The components of the device may be readily assembled into a usable unit by persons having little or no mechanical skill.

7 Claims, 5 Drawing Figures

U.S. Patent  June 22, 1976  3,965,008
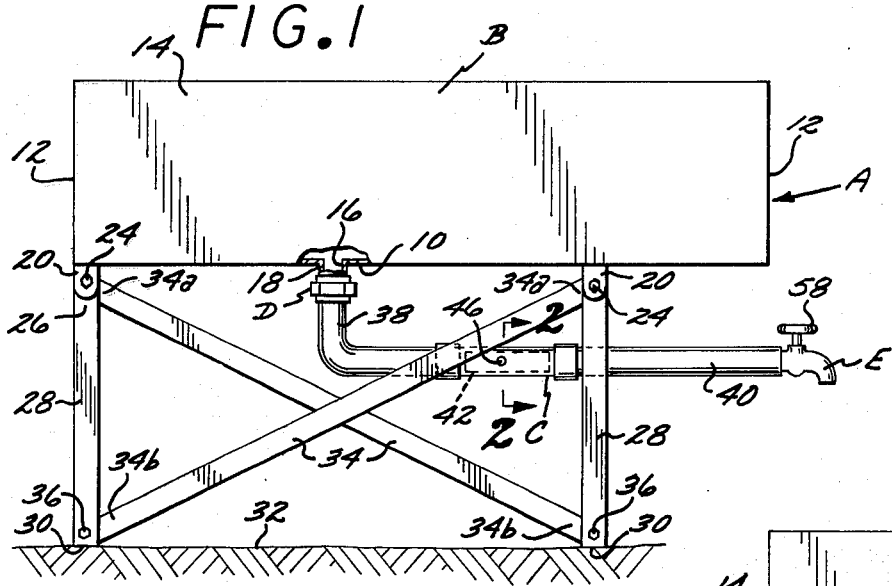
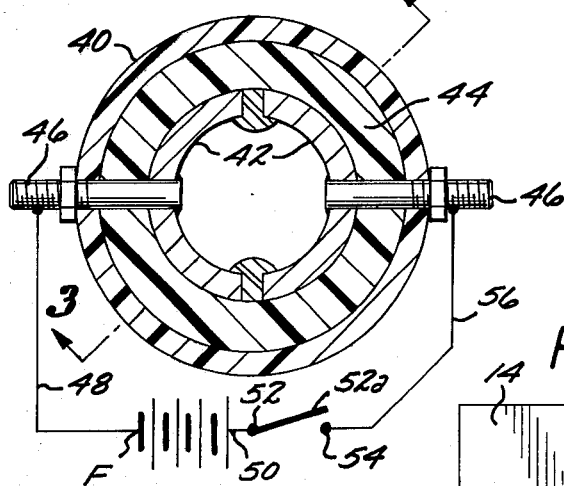
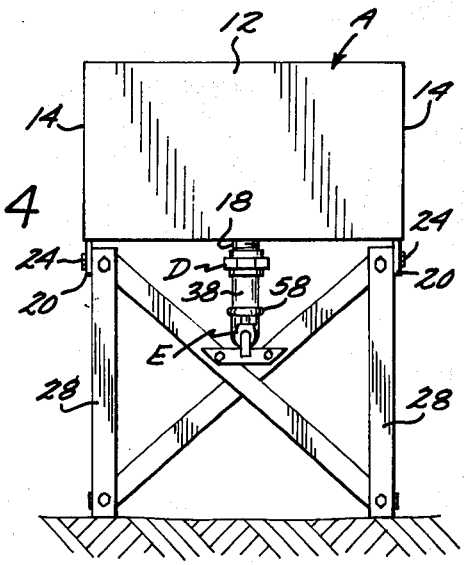
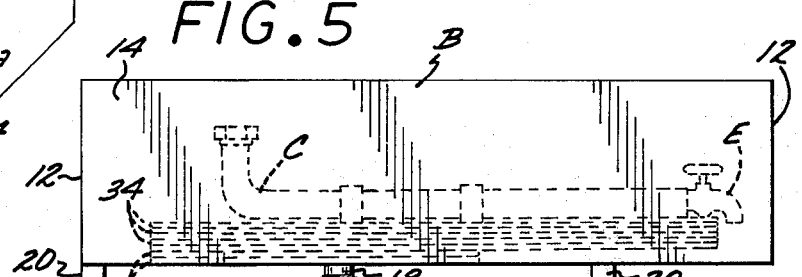
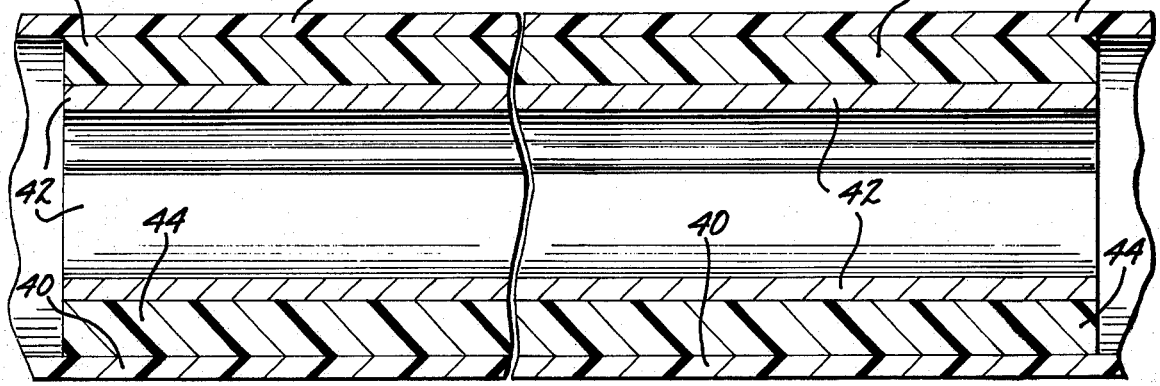

PORTABLE WATER STERILIZATION DEVICE

CROSS REFERENCE TO RELATED APPLICATION

The present invention is a continuation-in-part of my copending application, Ser. No. 451,576, filed Mar. 15, 1974, now abandoned, entitled WATER STERILIZATION METHOD AND APPARATUS.

BACKGROUND OF THE INVENTION

1. Field of the Invention
Portable Water Sterilization Device.
2. Description of the Prior Art In areas that have been subjected to disasters such as a flood, major fire, hurricane, earthquake and the like, the normal sources of drinking water become contaminated by sewage and the water is no longer potable. An essential requirement in such an area and one of top priority is to immediately provide a source of water that is free of harmful bacteria and is potable.

In the prior art numerous large scale water treatment systems are described in which the contaminated water is treated with such sterilizing agents as organic compounds, bromine, iodine, chlorine, ozone, peroxides, silver salts, lime and alkali agents by massive equipment. Such systems have little or no utility in a disaster area, where a relatively small amount of potable water must be provided in a minimum of time.

A major object of the present invention is to supply a water sterilization device that is light weight and compact and may be shipped in a knocked down condition to an area requiring potable water and assembled in minutes to provide a small scale source of potable water. The potable water so supplied is derived from contaminated, harmful bacteria containing water by subjecting the latter to alternating electric current, preferably at a potential of 220 volts.

SUMMARY OF THE INVENTION

The invention is a portable device for use in transforming harmful bacteria-contaminated water into potable water, with the device including a number of components tht are removably connected to one another and may be separated and stored in a compact space when the device is not in use, or when the device is being transported to an area where it will be used.

The invention includes a tank in which harmful bacteria-contaminated water may be placed, with the tank including a bottom in which a water discharge opening is defined, and a tubular boss extending outwardly from the bottom and in communication with the water discharge opening. A number of legs are provided, which legs by bolts or other means are removably secured to the tank to support the latter at an elevated position above the surface on which the legs rest. An inverted L-shaped tubular member that has first and second legs is provided, and by a coupling or other means, the first leg is removably secured to the tubular boss.

A manually actuable valve is secured to the free end of the second leg of the tubular member, with the valve capable of being manually adjusted to permit water from the tank to flow by gravity through the tubular member at not greater than a predetermined rate to discharge from the valve. Two laterally spaced, oppositely disposed, elongate electrodes are situated within the L-shaped tubular member at a position intermediate the ends thereof, with the electrodes electrically isolated from one another. Two terminals are provided for supplying alternating electric power to the electrodes at a voltage potential sufficient to kill harmful bacteria in the contaminated water, when the latter flows by gravity between the electrodes in the tubular member at not greater than the predetermined rate. The legs, L-shaped tubular member, and valve are of such dimension as to be storable within the confines of the tank when the device is not in use, or when the device is being transported to an area in which it will be used to transform contaminated harmful bacteria-containing water into potable water.

BRIEF DESCRIPTION OF THE DRAWING

FIG. 1 is a side elevational view of the device in an assembled form for transforming contaminated harmful bacteria-containing water into potable water;

FIG. 2 is a fragmentary transverse cross sectional view of a portion of the device taken on the line 2—2 of FIG. 1;

FIG. 3 is a fragmentary longitudinal cross sectional view of a portion of the device taken on the line 3—3 of FIG. 2;

FIG. 4 is an end elevational view of the device; and

FIG. 5 is a side elevational view of the device after the components thereof have been separated from one another and stored within the confines of the tank.

DESCRIPTION OF THE PREFERRED EMBODIMENT

The invention A for use in transforming contaminated harmful bacteria-containing water to potable water is shown in elevation in FIG. 1. The device A includes an elongate tank B, preferably of rectangular transverse cross section and one that is defined by a bottom 10, a pair of end walls 12, and a pair of side walls 14. A water discharge opening 16 is formed in the bottom 10, intermediate the ends thereof and is in communication with a tubular boss 18 that extends downwardly from the bottom. The boss 18 is illustrated as having external threads 18a thereon. The tank B preferably has two pairs of longitudinally spaced lugs 20 extending downwardly fron the side walls thereof, as shown in FIG. 1, with the lugs having apertures 22 therein. The apertures 22 are engaged by bolts 24, which bolts also engage apertured first ends 26 of legs 28. The second end 30 of the legs 28 rest on surface 32.

Two sets of longitudinally extending reinforcing members 34 are provided, with each set including two reinforcing members arranged in the form of a cross, with first end portion 34a of the reinforcing members being apertured and engaging the bolts 24 as shown in FIG. 1. The members 34 have apertured second end portions 34b that are engaged by bolts 36, which bolts also extend through apertures in the second end portion 30 of the legs 28.

An inverted tubular L-shaped member C is provided, which member includes a first leg 38 and second leg 40. Two elongate electrodes 42 of arcuate, transverse cross section are oppositely disposed within the tubular member C and situated intermediate the ends thereof. The electrodes 42 are held in fixed position within the confines of the tubular member C by a cylindrical body 44 of an electrical insulating material. The tubular member C is preferably formed from plastic or like material that is an electrical insulator. Two electrical terminals 46 are connected to the electrodes 42 and extend outwardly through the body of insulation 44 and the wall of the tubular member C.

In FIG. 2 it will be seen that an electrical conductor 48 is connected to one of the terminals 46 and extends to a source of alternating electrical power F, which source of power F is connected by a conductor 50 to a manually operable electric switch 52. The switch 52 includes a blade 52a that may be moved into engagement with a contact 54. An electrical conductor 56 extends from the contact 54 to one of the terminals 46 as shown in FIG. 2.

Valve E is mounted on the free end of the leg 40 of tubular member C, with the valve including a handle 58 that may be manually adjusted to allow contaminated water to flow by gravity from the tank B at not greater than a predetermined rate through the tubular member C. When the switch 52 is closed, an electrical potential zone of desired magnitude is established between the electrodes 42, and as contaminated water flows through this zone harmful bacteria in the water are killed and the water rendered potable. The voltage potential of the alternating electric current flowing between the electrodes 42 in this zone must be sufficient to kill harmful bacteria in the water during the time period that the water flows at not greater than a predetermined rate.

In FIG. 4 it will be seen that cross bracing 58 extends between the legs 28 and is removably secured thereto by bolts 60 or other conventional fastening means. When the invention A is operating, potable water discharges from the valve E into containers (not shown).

After the invention A has served to transform contaminated to potable water, the tank B is drained of water, and the tubular member C, coupling D, reinforcing members 34, legs 28 are separated from the tank B, with these components being of such size and configuration as to fit and be stored within the confines of the tank B as shown in phantom line in FIG. 5. The invention A in the knock-down condition shown in FIG. 5 may be stored in a compact space, or may be easily transported from one area to another to transform contaminated harmful bacteria containing water to potable water.

The use and operation of the invention has been explained previously in detail and need not be repeated.

I claim:

1. A portable device for use in transforming harmful bacteria contaminated water into potable water, said device including a plurality of components that are removably connected to one another and that may be separated and stored in a compact space when said device is not in use, said device including:
   a. a tank in which said harmful bacteria contaminated water may be placed, said tank including a bottom in which a water discharge opening is defined, and a tubular boss extending outwardly from said bottom and in communication with said water discharge opening;
   b. a plurality of legs each of said legs including first and second end portions;
   c. first means for removably securing said legs to said tank to support the latter at an elevated position above the surface on which said legs rest;
   d. an inverted L-shaped tubular member that has first and second legs;
   e. second means for removably securing said first leg to said tubular boss;
   f. a manually actuatable valve secured to said second leg, said valve capable of being manually adjusted to permit water from said tank to flow by gravity through said tubular member at not greater than a predetermined rate and discharge from said valve;
   g. two laterally spaced, oppositely disposed elongate electrodes situated in said L-shaped member at a position intermediate the ends thereof, with said electrodes electrically insulated from one another; and
   h. third means for supplying alternating electric power to said electrodes at a voltage potential sufficient to kill said harmful bacteria in said water when the latter flows between said electrodes in said tubular member at not greater than said predetermined rate, with said legs, L-shaped tubular members and valve of such dimensions as to be storable within said tank when said device is not in use.

2. A device as defined in claim 1 in which said tank is rectangular in shape and said legs are four in number and disposed as two longitudinally spaced pairs, and said first means includes:
   i. two pair of longitudinally spaced apertured lugs that project downwardly from said tank; and
   j. a plurality of bolts that engage said apertured lugs and aperatures in said first end portions of said legs to removably connect said legs to said tank to support the latter.

3. A device as defined in claim 2 which in addition includes:
   k. a plurality of longitudinally extending reinforcing members; and
   l. fourth means for removably securing said reinforcing members to said legs.

4. A device as defined in claim 2 which in addition includes:
   k. a plurality of transverse reinforcing members; and
   l. fourth means for removably securing said reinforcing members to said legs.

5. A device as defined in claim 1 in which said tubular boss and free end portion of said first leg of said tubular member have threads formed thereon, and said second means is a threaded coupling that removably engages said threads.

6. A device as defined in claim 1 in which in addition includes:
   k. two bodies of electrical insulating material that support said electrodes in fixed positions within the interior of said inverted L-shaped tubular member.

7. A device as defined in claim 6 in which said inverted L-shaped tubular member is formed from an electrical insulating material and said third means are two electrical conducting terminals connected to said electrodes, with said terminals extending outwardly in opposite directions through said bodies of electrical insulating material and said inverted L-shaped tubular member to the exterior of the latter.

* * * * *